US012169934B2

United States Patent
Nguyen et al.

(10) Patent No.: US 12,169,934 B2
(45) Date of Patent: Dec. 17, 2024

(54) REAL-TIME, ARTIFICIAL INTELLIGENCE-ENABLED ANALYSIS DEVICE AND METHOD FOR USE IN NUCLEAR MEDICINE IMAGING

(71) Applicant: University of Pittsburgh-Of the Commonwealth System of Higher Education, Pittsburgh, PA (US)

(72) Inventors: Nghi Nguyen, Allen, TX (US); Shandong Wu, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 392 days.

(21) Appl. No.: 17/805,126

(22) Filed: Jun. 2, 2022

(65) Prior Publication Data
US 2023/0129584 A1  Apr. 27, 2023

Related U.S. Application Data

(60) Provisional application No. 63/244,933, filed on Sep. 16, 2021.

(51) Int. Cl.
*G06T 7/20* (2017.01)
*A61B 6/40* (2024.01)
(Continued)

(52) U.S. Cl.
CPC .......... *G06T 7/0012* (2013.01); *A61B 6/4057* (2013.01); *A61B 6/4208* (2013.01);
(Continued)

(58) Field of Classification Search
CPC ..... A61B 6/037; A61B 6/4057; A61B 6/4208; A61B 6/469; A61B 6/488; A61B 6/5264;
(Continued)

(56) References Cited

U.S. PATENT DOCUMENTS 5,576,548 A * 11/1996 Clarke ................ G06T 5/60
  250/369
6,740,883 B1 * 5/2004 Stodilka ............ G01T 1/1648
  250/363.04
(Continued)

FOREIGN PATENT DOCUMENTS

CA  2721484 A1 * 11/2000  ............. A61K 31/46
CA  3085441 A1 *  7/2019  ............. A61B 6/032
(Continued)

OTHER PUBLICATIONS

Viktor Rogowski, "Feasibility of Dynamic SPECT—Renography with Automated Evaluation Using a Deep Neural Network," Jun. 8, 2021, Master of Science Thesis HT2020, Medical Physics Programme, Lund University, pp. 5-40.*
(Continued)

*Primary Examiner* — Omar S Ismail
(74) *Attorney, Agent, or Firm* — TaeRa Franklin; Eckert Seamans Cherin & Mellott, LLC

(57) ABSTRACT

A system, device and method of imaging using a real-time, AI-enabled analysis device coupled to an imaging device during an image scan of a subject includes: receiving data corresponding to a plurality of image frames from the imaging device and user input identifying a region of interest (ROI) in a first image frame; providing data corresponding to the first image frame, including the identified ROI and data corresponding to the remaining image frames to the AI-enabled data processing system; accepting a plurality of valid image frames from the plurality of image frames based on a predefined set of computer vision rules and a minimum accepted frame threshold; calculating, frame by frame, an ROI function value of the plurality of valid image frames; determining whether a predetermined ROI function value has been reached; and alerting an operator of
(Continued)

the imaging device that the predetermined ROI function value has been reached.

20 Claims, 11 Drawing Sheets

(51) Int. Cl.
*A61B 6/42* (2024.01)
*G06T 7/00* (2017.01)

(52) U.S. Cl.
CPC ...... *G06T 7/20* (2013.01); *G06T 2207/20081* (2013.01); *G06T 2207/20101* (2013.01); *G06T 2207/30004* (2013.01)

(58) Field of Classification Search
CPC .......... A61B 6/545; G06T 2207/10016; G06T 2207/10081; G06T 2207/10104; G06T 2207/10108; G06T 2207/20081; G06T 2207/20084; G06T 2207/20101; G06T 2207/20104; G06T 2207/30004; G06T 2207/30096; G06T 7/0012; G06T 7/0016; G06T 7/20
See application file for complete search history.

(56) References Cited

U.S. PATENT DOCUMENTS

| | | | | |
|---|---|---|---|---|
| 7,122,172 | B1* | 10/2006 | Graupner | A61K 51/088 424/9.4 |
| 9,050,378 | B2* | 6/2015 | Yang | A61K 51/0497 |
| 10,565,477 | B2 | 2/2020 | Hsieh et al. | |
| 10,803,984 | B2 | 10/2020 | Zhou et al. | |
| 2007/0203332 | A1* | 8/2007 | Graupner | A61K 41/0095 435/7.1 |
| 2010/0284920 | A1* | 11/2010 | Cheung | C07K 16/18 435/69.6 |
| 2012/0132814 | A1* | 5/2012 | Weinberg | G01V 5/26 250/362 |
| 2012/0220870 | A1* | 8/2012 | Gambhir | B82Y 30/00 600/431 |
| 2014/0161725 | A1* | 6/2014 | Morse | A61K 49/0021 424/9.4 |
| 2015/0051153 | A1* | 2/2015 | Reshetnyak | A61K 38/12 514/19.2 |
| 2018/0144214 | A1* | 5/2018 | Hsieh | G06T 7/0002 |
| 2018/0144243 | A1* | 5/2018 | Hsieh | G06F 11/30 |
| 2018/0144466 | A1* | 5/2018 | Hsieh | G16H 40/40 |
| 2020/0337658 | A1* | 10/2020 | Sjostrand et al. | G16H 30/40 |
| 2021/0270993 | A1* | 9/2021 | Cederwall | G01T 3/06 |

FOREIGN PATENT DOCUMENTS

| | | | |
|---|---|---|---|
| CN | 111655159 A | 9/2020 | |
| EP | 1105750 B1* | 10/2004 | ............ A61B 6/037 |
| JP | 2019082745 A | 8/2020 | |
| RU | 2698997 C1 | 9/2019 | |
| WO | WO-2008045952 A2* | 4/2008 | ......... A01K 67/0275 |

OTHER PUBLICATIONS

Qi Dou et al., "Automatic Detection of Cerebral Microbleeds From MR Images via 3D Convolutional Neural Networks," Apr. 29, 2016,IEEE Transactions On Medical Imaging, vol. 35, No. 5, May 2016, pp. 1182-1193.*
Pim Moeskops et al. ,"Automatic Segmentation of MR Brain Images With a Convolutional Neural Network," Apr. 29, 2016,IEEE Transactions On Medical Imaging, vol. 35, No. 5, May 2016, pp. 1-10.*
Sérgio Pereira et al., "Brain Tumor Segmentation Using Convolutional Neural Networks in MRI Images," Apr. 29, 2016,IEEE Transactions On Medical Imaging, vol. 35, No. 5, May 2016, pp. 1240-1249.*
Junji Shiraishi et al., "Computer-Aided Diagnosis and Artificial Intelligence in Clinical Imaging," Oct. 3, 2011, Seminars in Nuclear Medicine, vol. 41, Issue 6, Nov. 2011, pp. 449-459.*
Mehmet Günhan Ertosun et al., "Probabilistic Visual Search for Masses Within Mammography Images using Deep Learning," Dec. 17, 2015,2015 IEEE International Conference on Bioinformatics and Biomedicine (BTBM), pp. 1310-1314.*
Dou et al., "Automatic Detection of Cerebral Microbleeds From MR Images via 3D Convolutional Neural Networks", IEEE Transactions on Medical Imaging, vol. 35, No. 5, May 2016, 14 pages.
Ertosun et al., "Probabilistic Visual Search for Masses Within Mammography Images using Deep Learning", 2015 IEEE International Conference on Bioinformatics and Biomedicine (BIBM), 6 pages.
Moeskops et al., "Automatic Segmentation of MR Brain Images With a Convolutional Neural Network", IEEE Transactions on Medical Imaging, vol. 35, No. 5, May 2016, 11 pages.
Pereira et al., "Brain Tumor Segmentation Using Convolutional Neural Networks in MRI Images", IEEE Transactions on Medical Imaging, vol. 35, No. 5, May 2016, 12 pages.
Setio et al., "Pulmonary Nodule Detection in CT Images: False Positive Reduction Using Multi-View Convolutional Networks", IEEE Transactions on Medical Imaging, vol. 35, No. 5, May 2016, 10 pages.

* cited by examiner

| Easy Cases Subjects ID | 001 | 003 | 004 | 007 | 008 | 034 | 040 | 042 | 050 | 052 | Avg. |
|---|---|---|---|---|---|---|---|---|---|---|---|
| DICE of inter-reader agreement (avg. of DSC1) | 0.869 | 0.485 | 0.874 | 0.838 | 0.823 | 0.823 | 0.665 | 0.690 | 0.835 | 0.916 | 0.782 |
| DICE of H1 vs. AI segmentation | 0.836 | 0.744 | 0.867 | 0.893 | 0.876 | 0.894 | 0.782 | 0.634 | 0.654 | 0.867 | 0.805 |
| P-value of (DSC1, DSC2)(P1,2) | 0.938 | 0.870 | 0.985 | 0.834 | 0.897 | 0.857 | 0.766 | 0.975 | 0.649 | 0.780 | 0.893 |

FIG. 4A

| Difficult Cases Subjects ID | 060 | 063 | 069 | 071 | 074 | 076 | 078 | 082 | 087 | 089 | Avg. |
|---|---|---|---|---|---|---|---|---|---|---|---|
| DICE of inter-reader agreement (avg. of DSC1) | 0.844 | 0.498 | 0.835 | 0.844 | 0.830 | 0.755 | 0.854 | 0.849 | 0.837 | 0.626 | 0.777 |
| DICE of H1 vs. AI segmentation | 0.878 | 0.493 | 0.888 | 0.840 | 0.834 | 0.784 | 0.769 | 0.862 | 0.163 | 0.347 | 0.686 |
| P-value of (DSC1, DSC2)(P1,2) | 0.955 | 0.999 | 0.904 | 0.991 | 0.995 | 0.964 | 0.913 | 0.986 | 0.223 | 0.918 | 0.885 |

FIG. 4B

| Easy Cases Subjects ID | 001 | 003 | 004 | 007 | 008 | 034 | 040 | 042 | 050 | 052 | Avg. |
|---|---|---|---|---|---|---|---|---|---|---|---|
| Inter-reader agreement (avg. of DSC1) | 0.869 | 0.485 | 0.874 | 0.838 | 0.823 | 0.823 | 0.665 | 0.690 | 0.835 | 0.916 | 0.782 |
| H2 vs. AI's segmentation (ave. of DSC3) | 0.814 | 0.514 | 0.817 | 0.796 | 0.852 | 0.860 | 0.752 | 0.501 | 0.789 | 0.868 | 0.756 |
| P-value of (DSC1, DSC3)(P1,3) | 0.897 | 0.985 | 0.874 | 0.873 | 0.943 | 0.924 | 0.825 | 0.915 | 0.907 | 0.785 | 0.893 |

FIG. 5A

| Difficult Cases Subjects ID | 060 | 063 | 069 | 071 | 074 | 076 | 078 | 082 | 087 | 089 | Avg. |
|---|---|---|---|---|---|---|---|---|---|---|---|
| Inter-reader agreement (avg. of DSC1) | 0.844 | 0.498 | 0.835 | 0.844 | 0.830 | 0.755 | 0.854 | 0.849 | 0.837 | 0.626 | 0.777 |
| H2 vs. AI's segmentation (ave. of DSC3) | 0.265 | 0.767 | 0.782 | 0.797 | 0.693 | 0.693 | 0.579 | 0.760 | 0.054 | 0.595 | 0.596 |
| P-value of (DSC1, DSC3)(P1,3) | 0.334 | 0.920 | 0.901 | 0.888 | 0.857 | 0.857 | 0.725 | 0.899 | 0.157 | 0.991 | 0.756 |

FIG. 5B

REAL-TIME, ARTIFICIAL INTELLIGENCE-ENABLED ANALYSIS DEVICE AND METHOD FOR USE IN NUCLEAR MEDICINE IMAGING

CROSS-REFERENCE TO RELATED APPLICATIONS

This patent application claims the priority benefit under 35 U.S.C. § 119(e) of U.S. Provisional Application No. 63/244,933, filed on Sep. 16, 2021, the contents of which are herein incorporated by reference.

FIELD OF THE INVENTION

The disclosed concept relates generally to a system, device and method for imaging a subject, particularly, to a system, device, and method for real-time, AI-enabled image data analysis for use in nuclear medicine.

BACKGROUND OF THE INVENTION

Nuclear medicine is a subspecialty of radiology, that captures images of an organ, tissue, or structure of a patient using a radionuclide (e.g., radiopharmaceutical or radioactive tracer). The patient is injected with a small amount of a radioactive tracer, e.g., intravenously. Different tracer molecules are accumulated in different types of tissue, so an appropriate tracer is chosen that accumulates in the organ of interest, structure or region of interest (hereinafter, individually or collectively referred to as "ROI" unless specifically stated). The atom in the tracer molecule undergoes radioactive decay and produces gamma rays (photons) which emit from the patient. These gamma rays are detected by a gamma camera positioned outside of the patient. The output signals are received by a workstation (e.g., a PC, a laptop, a workstation used by an operator) and used for localizing and analyzing the radioactive tracers within the ROI during the image scan. For example, a level of ejection (e.g., ejection fraction of blood from a heart, ejection fraction of a radioactive tracer from a gallbladder, kidneys, etc.) of the radioactive tracer indicates a level of function of the organ or structure being examined. As such, while X-rays and ultrasounds provide anatomical information of the ROI, nuclear medicine studies provide functional information of an organ, which may be assessed via an ROI representing by organ in question.

Artificial intelligence (AI) is rapidly evolving in various fields of medicine. AI technology development, especially deep learning (DL), enables data-driven precision medicine. Among the AI applications in medicine, medical imaging shows great promise for imaging diagnosis, prognostication, and patient management. Radiomics, for example, is a method that extracts high-dimensional image features, either by traditional analytic methods or by convolutional neural networks (CNNs). It can be used for various clinical indications, including diagnosis and treatment monitoring. Machine learning (ML) is an important extension of AI, and traditional ML methods such as naïve Bayes, support vector machines, and random forests, have been widely used in medicine. In nuclear medicine, ML applications have so far involved disease diagnosis and prognosis as well as lesion classification, using tomographic imaging techniques, specifically positron-emission tomography (PET) and single-photon emission computed tomography (SPECT). More recently, deep learning methods such as CNNs and artificial neural networks (ANNs) have gained popularity because of the fast speed and better diagnostic performance than traditional ML. The use of such an AI is commonly done in two steps. First, the model is initially fit on a training dataset, which is used to fit the parameters of the AI model. The training step may include a supervised training which requires a user input, e.g., in determining ground truth. The AI model produces an initial result which is compared with the ground truth, for each vector in the training dataset. Depending on the result of the data comparison and AI algorithm being used, the parameters of the model are then adjusted. Subsequently, the fitted model can be used to predict the outcome of the observations in a second datasets called validation dataset. This validation dataset allows for an unbiased evaluation of the model fit on the training dataset while providing the opportunity for further tuning of the model.

In nuclear medicine, AI applications have been developed for tomographic datasets, capable of 3D image reconstruction, where data are obtained from a full 360-degree around the patient, either by rotation of the gamma camera around the patient or by a ring-detector positioned around the patient, specifically for SPECT and PET, which is analogous to CT. Most nuclear medicine studies however involve planar imaging, which is 2-dimensional analogous to a planar X-ray image. Planar image data may be acquired as a static view, at preset time or amount of radiotracer counts, or dynamically for a preset time, e.g., 60 min, following the administration of the radiotracer (e.g., intravenously). Dynamic studies are performed to examine how the amount of radiopharmaceutical or the shape of the organ changes with time. Statistics generated from ROIs placed in or around organs at various time frames of the dynamic study can be charted to display such changes graphically. The time-activity curve is the most common of these graphs. Current AI applications in nuclear medicine are designed for the data analyses of static 3D SPECT and PET data. They however lack features for dynamic image data evaluation with specific tasks for real-time tracking of and calculation of an ROI function or clearance, hereinafter, individually or collectively referred to as "ROI function" unless specifically stated, as detailed in embodiments of the present invention.

Current nuclear medicine image protocols for dynamic studies were established over 20 years ago, which are rigid, one-size-fits-all approaches, lacking the flexibility and option for process optimization. As an example, a recent retrospective study showed that most patients (88%) who had undergone a sincalide-stimulated cholescintigraphy achieved a normal gallbladder ejection fraction already by 30 minutes, indicating that the standard 60-minute cholescintigraphy was not necessary. The lengthy nuclear medicine imaging procedures are associated with patient discomfort, wasteful clinical resources, and decreased productivity. An AI-enabled imaging equipment may shorten the imaging workflow, meeting the clinical demands and greatly benefiting both patients and health care providers.

With the recent advances in computational technology and AI, advanced solutions for real-time tracking of and analyzing the radioactivity within specific organs are feasible. As demands for patient-centered patient care rise, radiology departments are called upon to improve efficiency and reduce cost while maintaining care quality. Recently, it has been acknowledged that improving scanner hardware and image quality is not sufficient and that innovations in imaging workflow, acquisition, and image interpretation are equally important. Moreover, there is an unmet need to innovate imaging workflows by introducing real-time data analyses and interventions to imaging procedures to advance the field of nuclear medicine. Thus, the use of real-time, AI-enabled (hereinafter, ML, AI, and ML/AI may be used interchangeably) data evaluation may improve the way scans are performed and analyzed at an individual level, depending on what is being discovered during the scan, such as pathologic findings or even patient movement. Real-time data analyses can function as clinical decision tools supporting the operator of the imaging device (e.g., technologists and radiologists) to perform a more effective and efficient job.

There is a need for improvement in imaging procedures, in particular nuclear medicine imaging procedures and equipment. Major vendors of imaging equipment are now making significant efforts to offer AI solutions for clinical decision support in medical imaging, but none has been able to offer imaging equipment that provides real-time, AI-enabled data analyses, which allow for an instantaneous interpretation (and interventions by the operators, if necessary) of nuclear medicine studies.

SUMMARY OF THE INVENTION

Accordingly, it is an object of the present disclosure to provide a novel system, device, and method for AI-enabled real time analysis for use during a dynamic nuclear medicine scan. The real-time, AI-enabled analysis system, device or methods in accordance with the present disclosure include four prongs: (i) training of an AI algorithm to track an object in nuclear medicine images based on dynamic, planar datasets; (ii) automatic tracking of an organ, a structure or a region of interest (hereinafter, individually or collectively referred to as "ROI", with an option for minimal user interaction, using computer vision on longitudinal imaging data of the organ; (iii) automatic and dynamic calculation of function values (e.g., ejection fraction values) during the scan; and (iv) real-time feedback to users with suggestions for intervention (e.g., stop the scan when normal values have been reached, or continue the scan if more data are required). That is, the real-time, AI-enabled analysis device, which has been previously trained to identify the ROI, automatically identifies and tracks the ROI and automatically and dynamically calculates ROI function values during the exam while providing instantaneous feedback and suggestions for intervention to the operator during the exam. During the imaging procedure, the human-machine interaction is kept to a minimum, and the human involvement may be limited to the initial ROI placement to define the ROI at the beginning of the scan and after completion of the autonomous data analyses. The built-in computer vision processes take into consideration possible flaws associated with AI algorithms. They probe and interpret the AI results dynamically image frame by image frame, and operate as gatekeepers in accepting or rejecting the AI results for individual image frames. The computer vision rules (e.g., a radiotracer count rule, a voxel count rule, etc.) are preset by the human expert readers who have studied the pattern of artifacts and errors associated with AI applications. Artifacts and errors are attributed to patient factors such as motion artifact and signal interference from organs or structures adjacent to the ROI. Only image frames deemed acceptable (valid image frames) may be used to calculate the ROI function values, such as ejection fraction or clearance within the ROI. If an image frame has been deemed an artifact or error, that frame may be excluded. The data output is updated instantaneously during the dynamic scan. Once the desired normal function threshold of a specific organ or structure, represented by the ROI, has been reached, e.g., ejection fraction is greater than or equal to 38% in the case of gallbladder evaluation, the real-time, AI-enabled analysis device provides a visual or sound alert, so that the technologist can review and confirm the AI results before stopping the scan.

The real-time, AI-enabled analytic system allows for the instantaneous and continuous display of imaging results on the computer screen and enables the operator to review the results and intervene instantaneously, if necessary, to correct for any quality issues. For example, data show significant artifact due to patient motion, resulting in suboptimal AI evaluation. Consequentially, the operator has the opportunity to communicate with the patient to control the undesirable patient motion and may override the AI-enabled results in case of severe motion artifacts, so the scan may continue to the end of the preset maximum scan duration. By accepting ROI data of valid image frames only, image frames with motion artifact are excluded from the ROI function calculation, which allows for a high-quality and efficient real-time data analysis. By alerting the operator upon satisfying the predefined ROI function threshold, the real-time analysis device enables the operator to stop the scan without having to continue the full standard scan (e.g., a 60-minute scan cholescintigraphy). For example, if the alert is made at, e.g., the 15-minute mark, and the operator determines that the scan results exhibit adequate quality, the operator may stop the image scan 45 minutes earlier than expected for the standard 60-minutes scan. As such, the real-time, AI-enabled analysis device can drastically shorten the scan time by providing real-time evaluation of organ functions and aiding the operator of the imaging device in the decision making to stop or continue the scan, dependent on the individual clinical scenario. In short, this novel analytic approach provides real-time data analyses at an individual level, which conforms to existing imaging workflows and image interpretation criteria, as well as can drastically improve procedure efficiency in terms of scan time and patient experience.

These objects are achieved according to embodiment of the present disclosure by providing an imaging system which includes: an imaging device structured to scan a subject during an image scan performed by an operator, the subject including an organ, a structure, or a region of interest (ROI) of the organ or the structure; a real-time, AI-enabled analysis device coupled to the imaging device and including an AI-enabled data processing system, an input apparatus, and a display, the real-time, AI-enabled analysis device configured to: receive data corresponding to a plurality of image frames from the imaging device and user input identifying an ROI in a first image frame of the plurality of the image frames; provide data corresponding to the first image frame, including the identified ROI and data corresponding to the remaining image frames to the AI-enabled data processing system, where the AI-enabled data processing system has been previously trained to automatically track the identified ROI during the image scan using training and test data representing a number of image datasets associated with the identified ROI obtained from a plurality of test subjects; accept a plurality of valid image frames from the plurality of image frames based on a predefined set of computer vision rules and a minimum accepted frame threshold; calculate, frame by frame, an ROI function value of the plurality of valid image frames; determine whether a predetermined ROI function value has been reached; and alert the operator of the imaging device that the predetermined ROI function value has been reached.

In some examples, the real-time, AI-enabled analysis device is further configured to receive a request to terminate the image scan from the operator based at least in part on the alert and a quality of scan results and terminate the image scan based on the request and display the scan results. In some examples, the real-time, AI-enabled analysis device is configured to accept the plurality of valid image frames by: setting the first image frame as a baseline image frame and the data corresponding to the first image frame including the identified ROI as baseline image frame data; setting an image frame immediately following the baseline image frame as a current image frame; automatically identifying the ROI in the current image frame using the AI-enabled data processing system; determining whether the current image frame satisfies the predefined set of computer vision rules; setting the data corresponding to the current image frame including the ROI as a current image frame data based on a determination that the current image frame satisfies the predefined set of computer vision rules; and accepting the current image frame as a valid frame image of the plurality of valid frame images based on the determination whether the current image frame satisfies the predefined set of computer vision rules. In some examples, the predefined set of computer vision rules includes a first predefined range associated with a radioactive tracer count within the ROI and a second predefined range associated with a voxel count within the ROI, and the real-time, AI-enabled analysis device is configured to accept the current image frame based on: a determination that the current image frame data is within the first predefined range associated with the radioactive tracer count within the ROI, and a determination that the current image frame data is within the second predefined range associated with the voxel count within the ROI. In some examples, the real-time, AI-enabled analysis device is further configured to: exclude the current image frame from calculating the ROI function value based on one of a determination that the current image frame data is not within the first predefined range and a determination that the current image frame data is not within the second predefined range; and set an image frame immediately following the current image frame as a new current image frame for at least one of automatically identifying the ROI in the new current image frame by the AI-enabled data processing system, accepting the new current image frame, or calculating the ROI function value. In some examples, the real-time, AI-enabled analysis device is further configured to set the current image frame as a new baseline image frame and the image frame immediately following the current image frame as a new current image frame based on a determination that the minimum accepted frame threshold is not met. In some examples, the ROI function value to be calculated includes at least one of an ejection fraction (EF) and a percentage clearance of radioactivity within the ROI. In some examples, the ROI function or clearance threshold includes a preset range of EF or clearance percentage of radioactivity based at least in part on a type of the image scan. In some examples, the real-time, AI-enabled analysis device is further configured to provide real time feedback comprising a frame-by-frame graphic display of time-activity curve, the ROI function value calculation, or real-time updates associated with the ROI function value calculation via the display. In some examples, the real-time, AI-enabled analysis device is couplable to at least one of a USB drive, a hard drive, or a cloud server for receiving AI-enabled real time analysis software application, software updates, or training data.

Another embodiment provides a real-time, AI-enabled real analysis device coupled to an imaging device for use during an image scan, including: an input apparatus, a display, and an AI-enabled data processing system, where the real-time, AI-enabled analysis device is configured to: receive data corresponding to a plurality of image frames from the imaging device and user input identifying an ROI in a first image frame of the plurality of the image frames; provide data corresponding to the first image frame, including the identified ROI and data corresponding to the remaining image frames to the AI-enabled data processing system, where the AI-enabled data processing system has been previously trained to automatically track the identified ROI during the image scan using training and test data representing a number of image datasets associated with the identified ROI obtained from a plurality of test subjects; accept a plurality of valid image frames from the plurality of image frames based on a predefined set of computer vision rules and a minimum accepted frame threshold; calculate, frame-by-frame, an ROI function value of the plurality of valid image frames; determine whether a predetermined ROI function value has been reached; and alert the operator of the imaging device that the predetermined ROI function value has been reached.

Another embodiment provides a method of imaging using a real-time, AI-enabled analysis device coupled to an imaging device during an image scan, including: receiving data corresponding to a plurality of image frames from the imaging device and user input identifying an ROI in a first image frame of the plurality of the image frames; providing data corresponding to the first image frame, including the identified ROI and data corresponding to the remaining image frames to the AI-enabled data processing system, where the AI-enabled data processing system has been previously trained to automatically track the identified ROI during the image scan using training and test data representing a number of image datasets associated with the identified ROI obtained from a plurality of test subjects; accepting a plurality of valid image frames from the plurality of image frames based on a predefined set of computer vision rules and a minimum accepted frame threshold; calculating, frame-by-frame, an ROI function value of the plurality of valid image frames; determine whether a predetermined ROI function value has been reached; and alerting an operator of the imaging device that the predetermined ROI function value has been reached.

In some examples, the method further includes receiving a request to terminate the image scan from the operator based at least in part on the alert and a quality of scan results; and terminating the image scan based on the request and displaying the scan results on a display of the AI-enabled real time analysis device. In some examples, accepting the plurality of valid image frames includes setting the first image frame as a baseline image frame and the data corresponding to the first image frame including the identified ROI as baseline image frame data; setting an image frame immediately following the baseline image frame as a current image frame; automatically identifying the ROI in the current image frame using the AI-enabled data processing system; determining whether the current image frame satisfies the predefined set of computer vision rules; setting the data corresponding to the current image frame including the ROI as a current image frame data based on the determination that the current image frame satisfies the predefined set of computer vision rules; and accepting the current image frame as a valid image frame of the plurality of valid image frames based on a determination whether the current image frame satisfies the predefined set of computer vision rules. In some examples, the predefined set of rules comprises a first predefined range associated with a radioactive tracer count within the ROI and a second predefined range associated with a voxel count within the ROI, and the accepting the current image frame is based on: a determination that the current image frame data is within the first predefined range associated with the radioactive tracer count within the ROI; and a determination that the current image frame data is within the second predefined range associated with the voxel count within the ROI. In some examples, the method further includes excluding the current image frame from calculating the ROI function value based on one of a determination that the current image frame data is not within the first predefined range and a determination that the current image frame data is not within the second predefined range; and setting an image frame immediately following the current image frame as a new current image frame for at least one of automatically identifying the ROI in the new current image frame by the AI-enabled data processing system, accepting the new current image frame, or calculating the ROI function value. In some examples, the method further includes setting the current image frame as a new baseline image frame and the image frame immediately following the current image frame as a new current image frame based on a determination that the minimum accepted frame threshold is not met. In some examples, the ROI function value to be calculated includes at least one of an ejection fraction (EF) of the ROI and a percentage clearance of radioactivity within the ROI. In some examples, the ROI function threshold includes a preset range of EF or clearance percentage based on a type of the image scan. In some examples, the method further includes providing real time feedback comprising a frame-by-frame graphic display of time-activity curve, the ROI function value calculation, or real-time updates associated with the ROI function value calculation via the display. In some examples, the real-time, AI-enabled analysis device is couplable to at least one of a USB drive, a hard drive, or a cloud server for receiving AI-enabled real time analysis software application, software updates, or training data.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 4A-5B illustrate feasibility study results using AI-enabled real time analysis system, device and method according to particular, non-limiting exemplary embodiments of the disclosed concept;

DETAILED DESCRIPTION OF EXEMPLARY EMBODIMENTS

Figure 1:
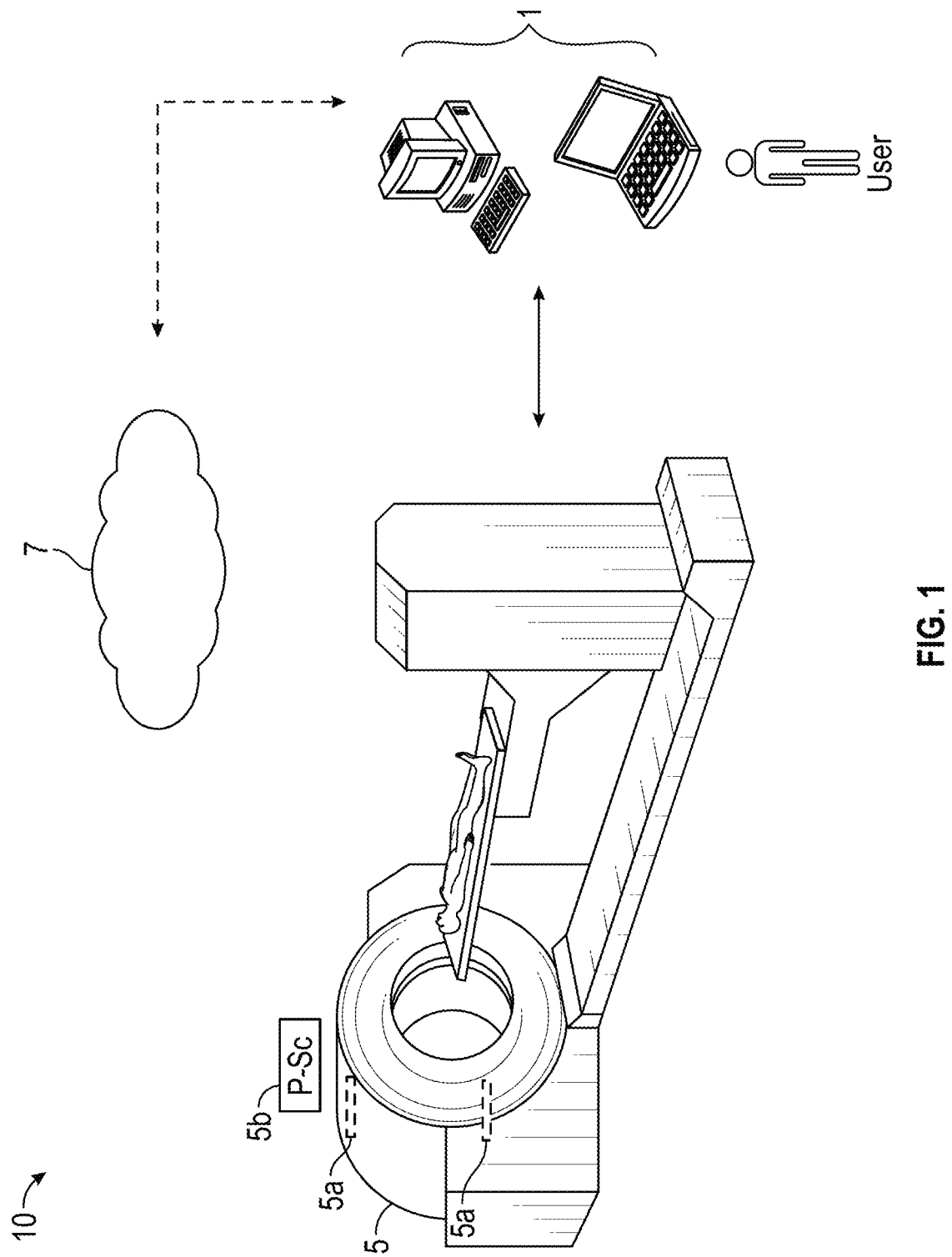
FIG. 1 illustrates an imaging system for AI-enabled real time analyses according to one particular, non-limiting exemplary embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the subject innovation. It will be evident, however, that the disclosed concept can be practiced without these specific details without departing from the spirit and scope of this innovation.

FIG. 1 illustrates an imaging system 10 for AI-enabled real time analysis of an image scan according to one particular, non-limiting exemplary embodiment of the disclosed concept. The imaging system 10 includes an AI-enabled real-time analysis device 1 and an imaging device 5 coupled to the AI-enabled real-time analysis device 1 via wired connection or wireless communications mechanisms (e.g., Bluetooth™, WiFi, LTE, etc.). As described with reference to FIG. 2 below, the AI-enabled real-time analysis device 1 includes an input apparatus 205, a display 210 and a control system 215, including an AI-enabled data processing system 220. The AI-enabled data processing system 220 may be codes, instructions, or software applications for AI-enabled real time analysis as described herein. The real-time, AI-enabled analysis device 1 may be communicatively coupled to a cloud server 7 for obtaining the codes, instructions, or software applications wirelessly, or coupled to a USB drive, hard disk, etc., containing the codes, instructions, or software applications to receive the codes, instructions, or software applications directly. A detailed explanation of the input apparatus 205, display 210 and the control system 215 is provided in connection with FIG. 2.

The AI-enabled real-time analysis device 1 may be any computer device (e.g., without limitation, a PC computer, a notebook computer, a mobile device, a workstation, etc.), and is configured to receive data corresponding to a plurality of image frames from the imaging device 5 and user input identifying an ROI in a first image frame of the plurality of image frames. The data corresponding to the plurality of image frames are captured by a gamma camera 5a of the imagine device 5, and the user input identifying the ROI may be a line drawn over the first image frame by the user (operator) using a persistence scope 5b. The p-scope 5b may be located on or at the imaging device 5, or be a part of the gamma camera 5a, showing radioactivity distribution within the ROI. Alternatively, the p-scope 5b may be located at or on the real-time, AI-enabled analysis device 1. The p-scope 5b is directly accessible by the operator via the display 210 of the AI-enabled real-time analysis device 1 such that the operator may draw the ROI directly on the received first image frame displayed on the display 210 using the input apparatus 205 (e.g., a mouse). The real-time, AI-enabled analysis device 1 is further configured to provide data corresponding to the first image frame, including the identified ROI, and data corresponding to the remaining image frames to the AI-enabled data processing system 220, where the AI-enabled data processing system 220 has been previously trained to automatically identify the ROI during the image scan in subsequent image frames using training and test data representing a number of image datasets associated with the ROI obtained from a plurality of test subjects. The AI-enabled data processing system 220 has been previously trained (e.g., via supervised or unsupervised AI training) using training and test data representing the parameters of the ROI obtained from a plurality of test subjects (e.g., patients being examined for the same or similar ROI) to identify the ROI using the ROI parameter. The number of test subjects vary according to a type of the image scan, radioactivity intensity, and quality of the training and test data. The training and test data may include any means of serial or dynamic data previously collected and saved on a suitable storage device (e.g., without limitation a USB drive, hard drive disk, optimal memory, or the cloud server 7).

The AI-enabled data processing system 220 is validated through two phases: a training phase and an evaluation phase. In the training phase, the AI-enabled data processing system 220 is trained to determine the parameters that optimally separates the event categories into, e.g., "signal" and "background" based on the signal and background sample data. In order to do this, a training dataset with human-identified ROIs (serving as ground truth) is provided to train a neural network model to separate the signal from the background. In the evaluation phase, a testing dataset also with human-identified ROIs (serving as ground truth) is used; the testing dataset is input to the trained neural network model to produce ROIs for the testing data, and then compare the produced ROIs to the human-identified ROIs using a metric of dice similarity coefficients. If the average of the dice similarity coefficients of the entire testing dataset is higher than a pre-defined threshold (this threshold may be preset by the operator based on clinical experience and it can be dynamically adjusted), then the trained model is claimed to be validated/useable/acceptable as the AI-enabled data processing system 220. If not, more training data will be supplied to re-train the model until it reaches the predefined threshold.

Once the training and evaluation is complete (the AI-enabled data processing system 220 is validated), the AI-enabled data processing system 220 evaluates uncategorized events (e.g., unanalyzed image frames or data representing unanalyzed image frames) using the determined (validated) ROI parameters, and classifies the uncategorized events into the ROI or the background. The real-time, AI-enabled analysis device 1 may receive instant updates from the on-going scan as well as any additional training and test data for continuous training.

The real-time, AI-enabled analysis device 1 is further configured to accept a plurality of valid image frames from the plurality of image frames based on a predefined set of computer vision rules and a minimum accepted frame threshold by: setting the first image frame as a baseline image frame and the data corresponding to the first image frame including the identified ROI as baseline image frame data; setting an image frame immediately following the baseline image frame as a current image frame; automatically identifying the ROI in the current image frame using the AI-enabled data processing system 220; determining whether the current image frame satisfies the predefined set of computer vision rules; setting the data corresponding to the current image frame including the ROI as a current image frame data based on the determination that the current image frame satisfies the predefined set of computer vision rules; and accepting the current image frame as a valid frame image of the plurality of valid frame images based on the determination that the current image frame satisfies the predefined set of computer vision rules.

The predefined set of computer vision rules may include, e.g., a first predefined range associated with a radioactive tracer count within the ROI and a second predefined range associated with a voxel count within the ROT. The predefined set of computer vision rules and computer vision processes in accordance with the predefined set of computer vision rules may be stored and/or built-into the real-time, AI-enabled analysis device 1. And a valid image frame must satisfy both the first predefined range and the second predefined range. The real-time, AI-enabled analysis device 1 is configured to accept the current image frame based on: a determination that the current image frame data is within the first predefined range associated with the radioactive tracer count within the ROI, and a determination that the current image frame data is within the second predefined range associated with the voxel count within the ROT. For example, the first predefined range may set forth a percentage (e.g., −20 to +7%) of the radioactive tracer count that the current image frame must meet as compared to the radioactive tracer count of the baseline image frame, and the second predefined range may set forth a percentage (e.g., −20 to +7%) of the voxel count that the current image frame must meet as compared to the voxel count of the baseline image frame.

The real-time, AI-enabled real time analysis device 1 may also be configured to exclude the current image frame from calculating the ROI function value based on one of the determination that the current image frame data is not within the first predefined range and the determination that the current image frame data is not within the second predefined range; and set an image frame immediately following the current image frame as a new current image frame for at least one of automatically identifying the ROI in the new current image frame by the AI-enabled data processing system 220, accepting the new current image frame, or calculating the ROI function value.

The real-time, AI-enabled analysis device 1 is further configured to set the current image frame as a new baseline image frame and the image frame immediately following the current image frame as a new current image frame based on a determination that the minimum accepted frame threshold is not met. The real-time, AI-enabled analysis device 1 may also accept the plurality of valid image frames based on the minimum accepted frame threshold, which may be a minimum number of the valid image frames to be considered for the ROI function calculation. For example, the minimum accepted frame threshold for ejection fraction calculation may be five or more valid image frames.

The real-time, AI-enabled analysis device 1 is further configured to calculate, frame by frame, an ROI function value of the plurality of valid image frames and determine whether a predetermined ROI function value has been reached. Upon meeting the minimum accepted frame threshold, the real-time, AI-enabled analysis device 1 may perform, frame-by-frame, the ROI function on those accepted valid image frames. The ROI function may be preset or predefined by the operator, dependent on the type of the image scan. For example, the predefined ROI function for a gallbladder image scan may include, e.g., without limitation ejection fraction (EF) of the ROI at any time interval (e.g., 15 minute, 20 minute, 30 minute, 40 minute, 45 minute, 60 minutes, etc.) and a half-time clearance of radioactivity within the ROI, which calculates EF at the half-time for clearing radioactivity within the ROI. Each of the accepted valid image frame is calculated for the EF value and upon reaching the valid image frame that satisfies the ROI function threshold, the real-time, AI-enabled analysis device 1 may alert the operator that the ROI function threshold has been met and the image scan may be stopped.

The ROI function threshold may include a predefined percentage of the ROI function value (e.g., gallbladder EF of ≥38% as normal, half-time clearance of renal radioactivity less than 12 minutes as normal, etc.), the percentage varying based on a type of the ROI being scanned and the exam being performed. If the predefined ROI function threshold is not reached by the last of, e.g., the five accepted valid image frame, the processing of the data of the next image frame continues and may continue until the minimum accepted frame threshold is met again and so forth. If the ROI function threshold is met by one of, e.g., the five accepted valid frames, the real-time, AI-enabled analysis device 1 may provide the operator a visual alert using the display 210 or audio alert using, e.g., a speaker (not shown), indicating that the ROI function threshold is met, and thus, the image scan may be stopped. The display 210 may also display, e.g., a frame-by-frame graphic display of time-activity curve, ROI function calculation, real-time updates as new calculation results become available, etc. Based on the visual and/or audible alert, the operator may review the scan result displayed on the display 210 and determine that the quality of the scan results are acceptable. The scan results may include the ROI for individual valid image frames and time-activity curve. If the ROI and the time-activity curve indicate that the valid image frames were of good image quality (i.e., minimal patient or organ motion artifacts and the ROI results are justified based on the ROI and the time-activity curve), the scan results are acceptable.

Based on his/her review of the scan results, the operator may enter via the input apparatus 205 or the display 210 (e.g., having a touch screen) requesting a prompt termination of the scan. If the scan results are not satisfactory, the operator may simply not input the request to terminate the image scan or input a request to continue the scan. The real-time, AI-enabled analysis device 1 is configured to receive the request to stop, and terminates the image scan based on the request to terminate. If the real-time, AI-enabled analysis device 1 does not receive the request to stop (or receives a request to continue the scan), the real-time, AI-enabled analysis device 1 continues the image scan. For example, if the operator deems that the result of the real-time, AI-enabled analysis device 1 is not satisfactory, the scan continues with concomitant AI analyses until the preset scan duration has reached or the operator decides to stop the scan based on the continuous AI data analyses. Continuing the image scan includes automatically identifying the ROI in the current image frame (e.g., additional image frames received from the imaging device 1) using the AI-enabled data processing system 220, accepting a plurality of valid image frames based on the predefined set of rules and the minimum accepted frame threshold; calculating, frame by frame, an ROI function value of the plurality of valid image frames; determining whether a predetermined ROI function value has been reached; and alerting the operator of the imaging device 1 that at least one of the predetermined ROI function value or a predefined maximum duration has been reached. The predefined maximum scan duration may depend on the type of the image scan, and generally be 60 minutes. The image scan continues until a valid image frame satisfies the ROI function threshold or the end of 60 minute-scanning. In some examples, the real-time, AI-enabled analysis device 1 may store the scan results including the image frames and the ROI function calculations in an internal or external memory and/or receive updates or additional training data from the cloud server 7 or the USB drive. Using the stored scan results and additional updates/training data, the AI-enabled data processing system 220 is continuously trained (unsupervised or supervised), thereby continuously refining the structure and parameters for identifying the ROI and background. The real-time, AI enabled analysis device 1 may be further configured to receive a request from the operator to terminate the image scan prior to reaching the predefined maximum scan duration, independently from the real-time, AI-enabled data analysis based on the sole decision of the operator or dependent on scan result output and the alert from the real-time, AI-enabled analysis device 1.

The imaging device 5 may be any suitable nuclear medicine and/or molecular imaging equipment, e.g., positron emission tomography (PET) used for detecting and diagnosing tumors and metastases by injecting radioactive tracer (e.g., fluorodeoxyglucose(FDG)) into a patient, PET-related Single Photon Emission Computer Tomography (SPECT) used for functional imaging by injecting a radioactive tracer (e.g., 99mTC-Methoxyisobutylisonitril) into the patient for detection and diagnosis of inflammation, tumors, and their metastases, PET or SPECT device used with a computed tomography (CT) for diagnosis and detection of tumors, etc. The imaging device 5 is a radiation detector such as radiation sensitive gamma cameras 5a for scintigraphic imaging. A gamma camera 5a captures the radioactivity within the ROI in real time. As such, the gamma camera in conjunction with the AI-enabled real time data analysis device 1 tracks the ROI and displays in real time the radioactive tracer distribution within the ROI on the display 210. Scintigraphy is a technique that uses radioisotopes in conjunction with the gamma camera to image functional processes and dynamic activities within the human body. The gamma camera 5a displays pixel intensities which reflect the local radioactive tracer accumulation or activities of a specific organ or ROI in question. As such, the gamma camera generates the data (e.g., without limitation radioactive tracer counts, voxel counts, etc.) that are used for determining whether any image frame received from the imaging device 1 should be accepted or rejected for calculating an ROI function in accordance with the present disclosure. The p-scope 5b is connected to the imaging device 5 and directly accessible by the operator. The operator may provide user input to the real-time, AI-enabled analysis device 1 by drawing a line using the p-scope 5b via the input apparatus 205 (e.g., a mouse) over the first image frame captured by the gamma camera 5a.

The imaging device 5 is structured to scan the ROI, acquire data representing the plurality of image frames captured during the image scan, and transfer real time the data to the real-time, AI-enabled analysis device 1 while the data acquisition is ongoing. The image frame rate (e.g., in seconds or minutes) and maximum number of frames as the maximum duration of the scan are set by the user (the operator), dependent or independent from the software development recommendations. These data and other training data, processed or not, are provided to the AI-enabled data processing system 220 for AI-enabled data processing (e.g., identifying the ROI and the background for each image frame received from the imaging device 1).

The cloud server 7 may be a data server storing the AI-enabled real time analysis software application, updates, and/or training and test data for the ROI. The cloud server 7 may be a propriety to a vendor of imaging equipment including the AI-enabled data processing system 220, or medical institutions using, leasing, or licensing such imaging equipment.

The interactive, real-time AI-enabled data analysis device 1 in accordance with the present disclosure engenders unprecedented flexibility, efficiency, and accuracy to the nuclear imaging workflow, allowing for individualized quantifications of organ functions. The real-time, AI-enabled analysis device 1 has the potential to revolutionize the way nuclear medicine data are being acquired and processed, as well as improve procedure efficiency and quality patient care. In some examples, the real-time, AI-enabled analysis device 1 may predict potential diagnosis, metastasis status, etc. based only on the real-time analysis of image data after a radioactive tracer has been administered to a patient.

Figure 2:
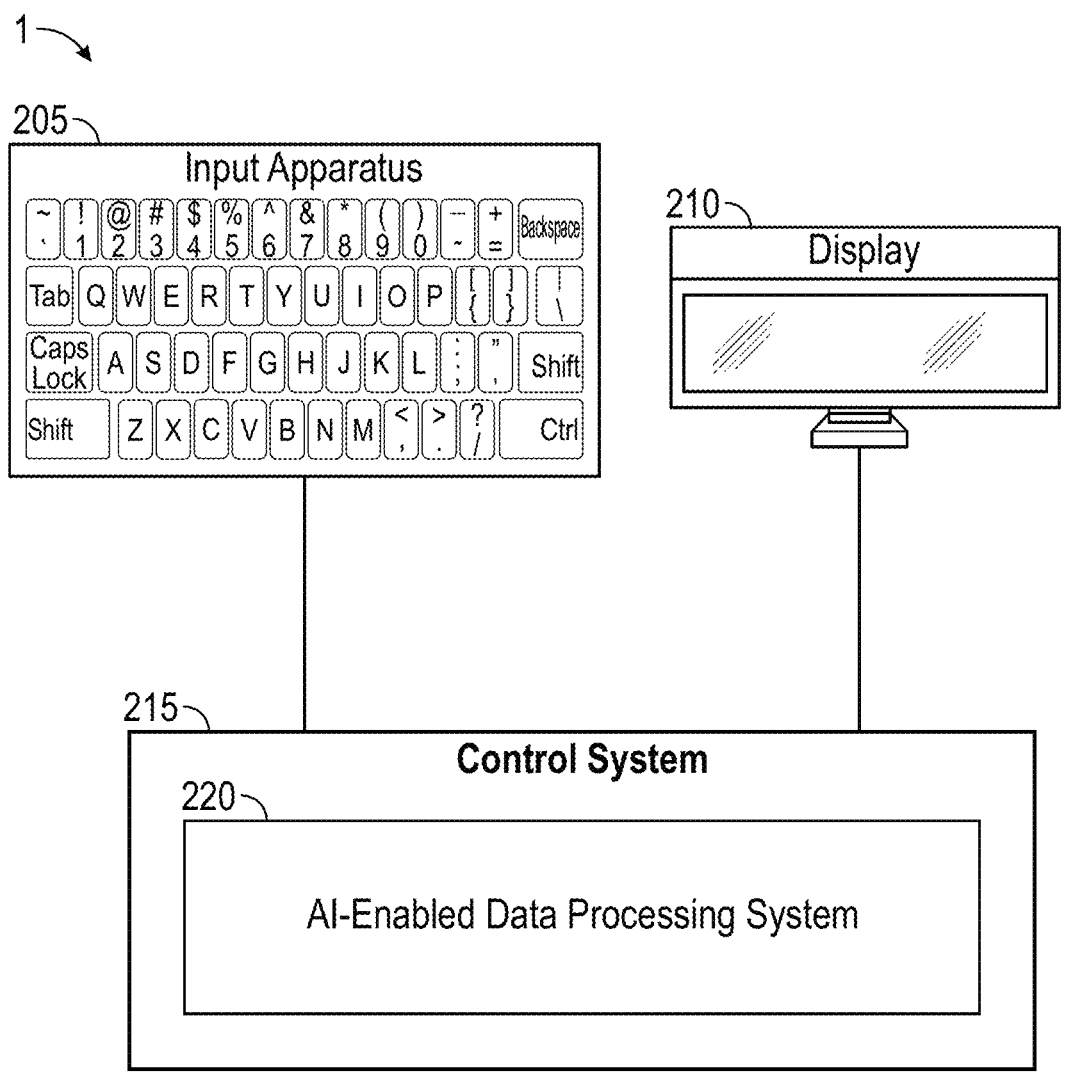
FIG. 2 illustrates a block diagram of an AI-enabled real time analysis device according to one particular, non-limiting exemplary embodiment of the disclosed concept.

FIG. 2 is a block diagram of an AI-enabled real-time analysis device 1 according to one particular, non-limiting exemplary embodiment. As seen in FIGS. 1 and 2, the exemplary AI-enabled real-time analysis device 1 is a PC or laptop computer and includes an input apparatus 205 (which in the illustrated embodiment is a keyboard), a display 210 (which in the illustrated embodiment is an LCD), and a control system 215. A user is able to provide input into the control system 215 using the input apparatus 205, and the control system 215 provides output signals to display 210 to enable the display 210 to display real time information to the operator, such as, without limitation, the data corresponding to the image frames being analyzed, the ROI function values of the valid image frames, whether an ROI function threshold is met, an alert that the ROI function threshold is met and the image scan can be stopped, etc.

Control system 215 includes a processor and a memory. The processor may be, for example and without limitation, a microprocessor (μP), a microcontroller, or some other suitable processing device, that interfaces with the memory. The memory can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. The memory has stored herein a number of routines, instructions, or codes that are executable by the processor. One or more of the routine implement (by way of computer/processor executable instructions) at least one embodiment of the method discussed in detail herein for AI-enabled real time data processing and analysis. The method is described in detail with reference to FIG. 3.

Figure 3A:
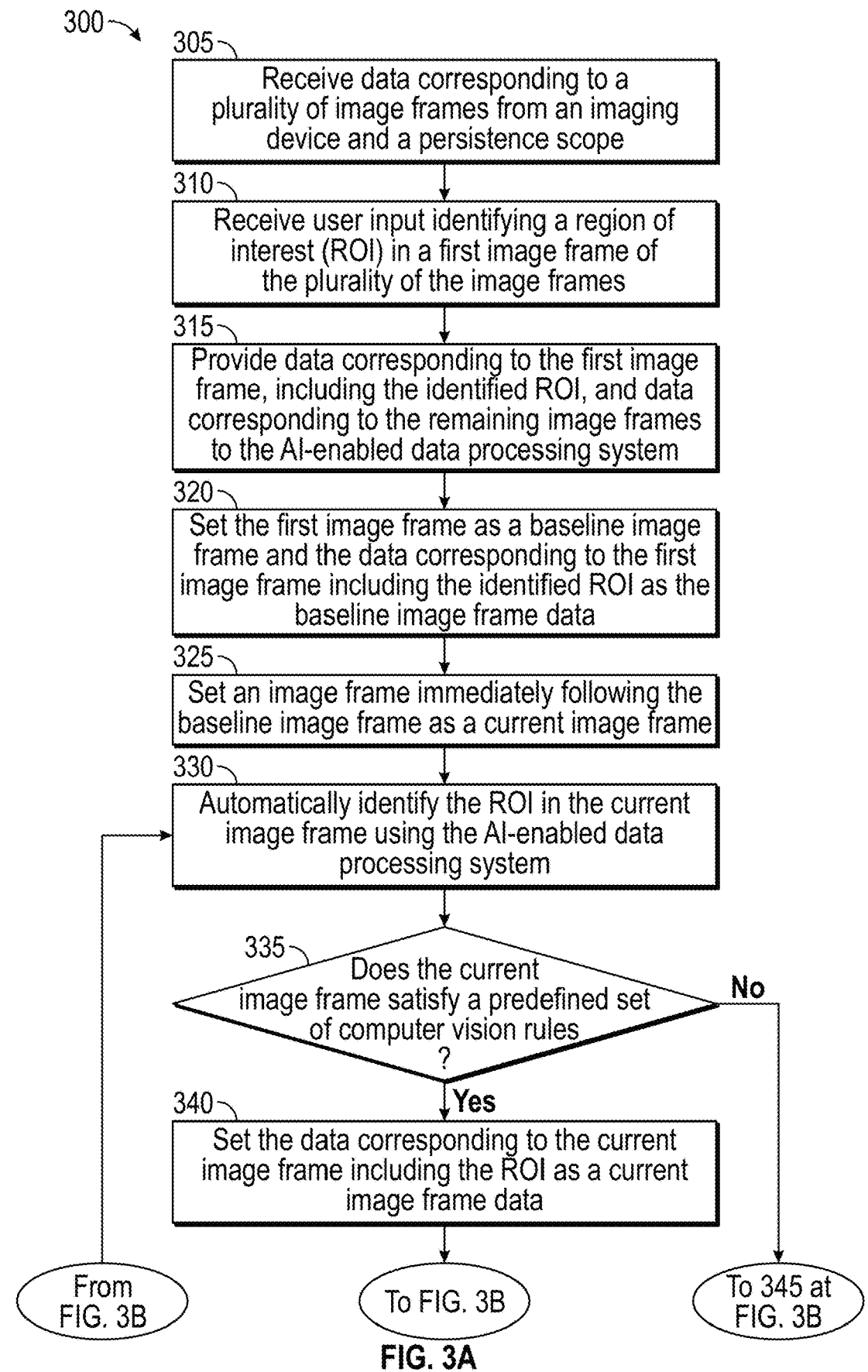
FIGS. 3A-B show a flow chart for a method of AI-enabled real time analysis for an image scan according to one particular, non-limiting exemplary embodiment of the disclosed concept.
Figure 3B:
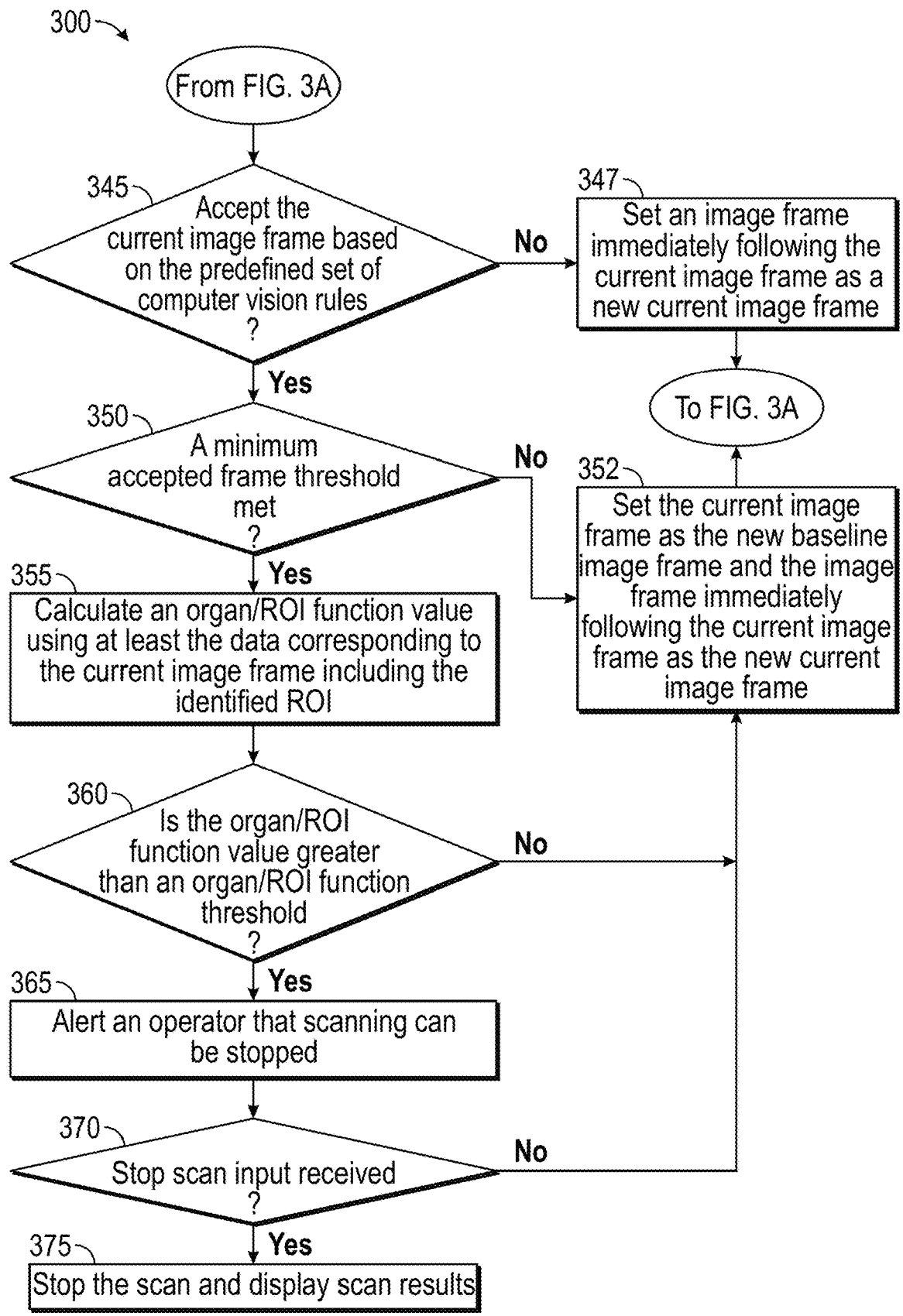

FIGS. 3A-B show a flow chart for a method of AI-enabled real time analysis for an image scan according to one particular, non-limiting exemplary embodiment of the disclosed concept. The method 300 is performed by the real-time, AI-enabled analysis device 1 as described with reference to FIG. 1-2, or any components thereof.

At 305, the real-time, AI-enabled analysis device 1 receives data corresponding to a plurality of image frames from an imaging device and a persistence scope. The images frames may be captured by a gamma camera 5a of an imaging device 5. The plurality of image frames include the image frames of an organ, a structure, or a region of interest (hereinafter, individually and/or collectively referred to as "ROI") of the organ or structure captured during the image scan of a subject (e.g., a patient), and may show any changes (e.g., without limitation ejection fraction, an organ photon counts, etc.) associated with the ROI during the scan.

At 310, the real-time, AI-enabled analysis device 1 receives user input identifying the ROI in a first image frame of the plurality of the image frames. User input is provided while the p-scope 5b is showing real time the overall radiotracer distribution of the ROI to be examined. The radiotracer activity has been administered to the patient some time before data acquisition (any time between a few seconds, a few hours, or a few days). Using the p-scope 5b as an image guidance, the user may draw or place two ROIs, one for the organ and one for the background, whose location depends on the type of the scan being performed. For example, the background may be placed in the right liver lobe for a hepatobiliary scan and inferolateral to the kidneys in a renal scan.

At 315, the real-time, AI-enabled analysis device 1 provides data corresponding to the first image frame, including the identified ROI, and data corresponding to the remaining image frames to the AI-enabled data processing system 220. That is, upon the completion of the ROI placements, the user or operator activates or starts the AI-enabled data processing system 220, which uses the user input as a guidance to identify the ROI. The AI-enabled data processing system 220 has been previously trained to identify and track the ROI using training and test data representing the structure and parameters of the ROI and the background obtained from a plurality of test subjects. The number of test subjects depend on the type of ROI and the exam being performed.

At 320, the real-time, AI-enabled analysis device 1 sets the first image frame as a baseline image frame and the data corresponding to the first image frame including the identified ROI as the baseline image frame data.

At 325, the real-time, AI-enabled analysis device 1 sets an image frame immediately following the baseline image frame as a current image frame.

At 330, the real-time, AI-enabled analysis device 1 automatically identifies the ROI in the current image frame using the AI-enabled data processing system 220.

At 335, the real-time, AI-enabled analysis device 1 determines whether the current image frame satisfies a predefined set of computer vision rules. The predefined set of computer vision rules may include, e.g., a first predefined range associated with a radioactive tracer count within the ROI and a second predefined range associated with a voxel count within the ROI. A valid image frame must satisfy both the first predefined range and the second predefined range. The real-time, AI-enabled analysis device 1 is configured to accept the current image frame based on: a determination that the current image frame data is within the first predefined range associated with the radioactive tracer count within the ROI, and a determination that the current image frame data is within the second predefined range associated with the voxel count within the ROI. For example, the first predefined range may set forth a percentage (e.g., −20 to +7%) of the radioactive tracer count that the current image frame must meet as compared to the radioactive tracer count of the baseline image frame, and the second predefined range may set forth a percentage (e.g., −20 to +7%) of the voxel count that the current image frame must meet as compared to the voxel count of the baseline image frame. If no, the method 300 proceeds to 345 and at 345 the real-time AI-enabled analysis device determines not to accept the current image frame and excludes the current image frame, and then the method 300 proceeds to 347. If yes, the method 300 proceeds to 340.

At 340, the real-time, AI-enabled analysis device 1 sets the data corresponding to the current image frame including the ROI as a current image frame data.

At 345, the real-time, AI-enabled analysis device 1 determines whether to accept the current image frame for a predefined ROI function calculation based on the predefined set of computer vision rules. If no, at 347 the real-time, AI-enabled analysis device 1 sets an image frame immediately following the current image frame as a new current image frame, and the method 300 returns to 330. If yes, the method 300 proceeds to 350. In determining whether to accept the current image frame, the real-time, AI-enabled analysis device 1 follows the predefined set of computer vision rules and the computer vision process in accordance with the predefined set of computer vision rules, the computer vision rules and process stored, included and/or built-in within the real-time, AI-enabled analysis device 1 (e.g., without limitation the control system 215). For example, for a gallbladder scanning, the predefined set of computer vision rules may include satisfying predefined ranges associated with radioactive tracer counts and voxel counts within the ROI. First, the AI-enabled real time analysis device 1 obtains a radioactive tracer count within the ROI of the current image frame. If the radioactive tracer count of the current image frame is within a first predefined range (e.g., −20% to +7%) of the radioactive tracer counts of the baseline image frame, the AI-enabled real-time analysis device 1 accepts the current image frame for further analysis. If the radioactive tracer counts of the current image frame is not within the first predefined range, the real-time, AI-enabled analysis device 1 labels the current image frame as invalid and excludes the current image frame from further analysis, and at 347 the real-time, AI-enabled analysis device 1 sets an image frame immediately following the current image frame as a new current image frame, and then the method 300 returns to 330. Next, the real-time, AI-enabled analysis device 1 obtains a number of voxels within the ROI for the current image frame that has been accepted for further processing. If the voxel count of the current image frame is within a second predefined range (e.g., −20% to +7%) of the voxel count of the baseline image frame, the current image frame is accepted for the predefined ROI function calculation and the method 300 proceeds to 350. If the voxel count of the current image frame does not satisfy the second predefined range, the AI-enabled real-time analysis device 1 labels the current image frame as invalid and excludes the current image frame from further process, and at 347 the real-time, AI-enabled analysis device 1 sets an image frame immediately following the current image frame as a new current image frame, and then the method 300 returns to 330. As such, to constitute a valid image frame for the predefined ROI function calculation, the current image frame must satisfy all computer vision rules, e.g., the first predefined range of radiotracer counts and the second predefined range of voxel counts. The predefined ROI function calculation depends on the type of the scan and exam being performed.

At 350, the real-time, AI-enabled analysis device 1 determines whether a minimum accepted image frame threshold is met. The minimum accepted frame threshold may be, e.g., a total of 5 valid image frames which may be deemed sufficient for an ROI organ function by the operator. If the minimum accepted frame threshold is met, the method 300 proceeds to 355. If not, at 352 the real-time, AI-enabled analysis device 1 sets the current image frame as the new baseline image frame and the image frame immediately following the current image frame as the new current image frame, and then the method 300 returns to 330.

At 355, the real-time, AI-enabled analysis device 1 calculates an ROI function value using at least the data corresponding to the current image frame including the identified ROI. The ROI function to be calculated may be preset or predefined by the operator. In the example involving the gallbladder scan, the predefined ROI function calculation may include, e.g., an ejection fraction (EF) calculation and a clearance calculation. The EF and the clearance may be calculated for each accepted frame, based on predefined settings by the operator according to the type of the nuclear medicine procedure being performed. The default settings may be predefined and/or modified by the user and determine at what image frame the EF calculation or the clearance calculation starts, dependent on the type of the procedure. The EF or clearance calculations may be based on ROI counts of peak counts (peak counts), ROI counts of current frame (current counts), and background counts at peak frame, and current frame (background peak counts; background current frame), adjusted for radioactive tracer delay over time. An example of EF calculation at a frame (e.g., a frame number 10) may be:

$$\frac{[\text{frame (peak) organ counts} - \text{frame (peak) background counts}] -}{[\text{frame No.10 organ counts} - \text{frame No.10 background counts}]} \qquad \text{EQ. 1}$$
$$[\text{frame (peak) organ counts} - \text{frame (peak) background counts}] \times 100$$

When calculating EF or clearance, only the accepted valid frames that have met the predefined set of computer vision rules, e.g., ranges for the radioactive tracer counts and the voxel counts between baseline and current image frames. In some examples, EF or clearance calculation may not start until the minimum accepted image frame threshold is met, and, e.g., without limitation a total of five image frames are available. In some examples, the EF or clearance is mathematically determined based on fitting of the time-activity curve. The form of the time-activity curve allows the computer software to fit a mathematical function to the curve. The most common functions fitted to time-activity curve are lines, exponentials, and cosines. Various physiologic parameters can be extracted from this time-activity curve analysis, including EF and half-time (T½) clearance. Half-time (T½) clearance is the time required for the radioactivity to fall by half from its maximum. The equation for exponential curve fit has the following form: Counts in ROI at time t=Maximum counts$\times e^{(-kt)}$, where k is the rate constant, which describes how fast a radiopharmaceutical is cleared or washes out of an ROI or organ.

At 360, the real-time, AI-enabled analysis device 1 determines whether the ROI function value is greater than an ROI function threshold. The ROI function threshold may vary based on the type of scan or exam being performed. In the example involving the gallbladder scan, the ROI function threshold for EF calculation may be, e.g., without limitation ≥38%. If the ROI function threshold is not met, the method 300 proceeds to 352 and the real-time, AI-enabled analysis device 1 sets the current image frame as the new baseline image frame and the image frame immediately following the current image frame as the new current image frame, and then the method 300 returns to 330. If yes, the method 300 proceeds to 365.

At 365, the real-time, AI-enabled analysis device 1 alerts the operator that the scanning can be stopped. The alert may be made on the display 210 or via a speaker. Upon receiving the alert, the operator may review the scan results displayed on the display 210, and determine whether the quality of the scan results are acceptable. The scan results may include the ROI for individual valid image frames and time-activity-curve. If the ROI and the time-activity-curve indicate to the operator, that there are no significant artifacts (from the patient or adjacent organ radioactivity) and the EF or clearance calculations are justified based on the ROI and the time-activity curve, the scan results are acceptable. Based on his/her review of the scan results, the operator may enter via the input apparatus 205 or the display 210 (e.g., having a touch screen) requesting a prompt termination of the scan. If the scan results are not satisfactory, the operator may simply not input the request to terminate the image scan or input a request to continue the scan.

At 370, the real-time, AI-enabled analysis device 1 determines whether a stop scan input is received. If no, the method 300 proceeds to 352. If yes, the method 300 proceeds to 375.

At 375, the real-time, AI-enabled analysis device 1 stops the image scan and displays scan results.

FIGS. 4A-5B illustrate feasibility study results using an AI-enabled real time analysis device and method according to particular, non-limiting exemplary embodiments of the disclosed concept. The feasibility study was conducted to establish and validate the real-time, AI-enabled analysis method and device. The autonomous and real-time identification and tracking of the organ ROI has been established and the initial attempt of instantaneous organ function calculation with built-in computer vision rules has been made. The successful tracking of the ROI as well as separation of the ROI from the surrounding artifacts was used to evaluate the system capabilities for real-time ROI tracking and function calculation. Validation analyses indicate that the system provides good diagnostic performance with a DICE similarity coefficient of approximately 0.8. For example, an AI-enabled real time analysis device and method in accordance with the present disclosure were used to automatically track, e.g., a gallbladder during the dynamic imaging scan. In this feasibility study, there was an acceptable agreement between two human readers (H1 and H2), with averaged dice similarity coefficient (DSC) of 0.782 for easy cases and 0.777 for difficult cases. For AI against H1, the DSC was 0.805 for easy cases and 0.686 for difficult cases. The DSC was not statistically significantly different between human readers (H1 vs. H2) and AI vs. H1 (P=0.918). For AI against H2, the DSC was 0.756 for easy cases and 0.596 for difficult cases. The DSC was not statistically significantly different between human readers (H1 vs. H2) and AI vs. H2 (P=0.991). The findings indicate that automatic tracking may provide objective reading similar to human readers. The real-time, AI-enabled analysis device and method also performed dynamic ejection fraction calculations in this feasibility study. Based on the initial visual assessment of 10 patient cases, the calculated ejection fraction trajectories and profiles were close to the truth data. FIGS. 4A-5B show the evaluation of an agreement between masks using dice similarity coefficient (DSC): where DSC=1 means that two masks are identical with each other, DSC=0 means that there is no intersection between two masks, and where DSC is greater than or equal to zero and less than or equal to 1, the larger the DSC the better the agreement. FIGS. 4A-5B compare three sets of DSCs with p-values: an inter-agreement (H1 segmentation v. H2 segmentation) denoted as $DSC_1$, H1 segmentation vs. AI predicted segmentation, denoted as $DSC_2$, and H2 segmentation vs. AI predicted segmentation, denoted as $DSC_3$. For each patient, two P-values are computed using the T-test statistics: P-value (DSC1, DSC2) of 60 slices for $DSC_1$ and for $DSC_2$, denoted as $P_{1,2}$, and P-value ($DSC_1$, $DSC_3$) of 60 slices for $DSC_1$ and for $DSC_3$, denoted as $P_{1,3}$.

FIGS. 4A-B show results 410 of easy cases and 420 of difficult cases, the results including DICE of inter-reader agreement, DICE of human reader H1 vs. AI segmentation, and P-values. Each number reported in $DSC_1$ and $DSC_2$ is an average over 60 slices for a subject (e.g., a patient's gallbladder). Each P-value ($P_{1,2}$) is computed from $DSC_1$ and $DSC_2$, both of 60 slices. P-value for all twenty patient's sixty slices of $DSC_1$ and $DSC_2$ is 0.918. There was no significant difference between AI's performance and H2 segmentation with respect to H1 segmentation. FIGS. 5A-B show results 510 of easy cases and results 520 of difficult cases, the results including inter-reader agreement, human reader H2's segmentation vs. AI's segmentation, and P-values. Each number reported in $DSC_1$ and $DSC_3$ is an average over 60 slices for a subject (e.g., a patient's gallbladder). Each P-value ($P_{1,3}$) is computed from $DSC_1$ and $DSC_3$, both of 60 slices. P-value for all twenty patient's sixty slices of $DSC_1$ and $DSC_3$ is 0.918. There was no significant difference between AI's performance and H1 segmentation with respect to H2 segmentation.

Figure 6:
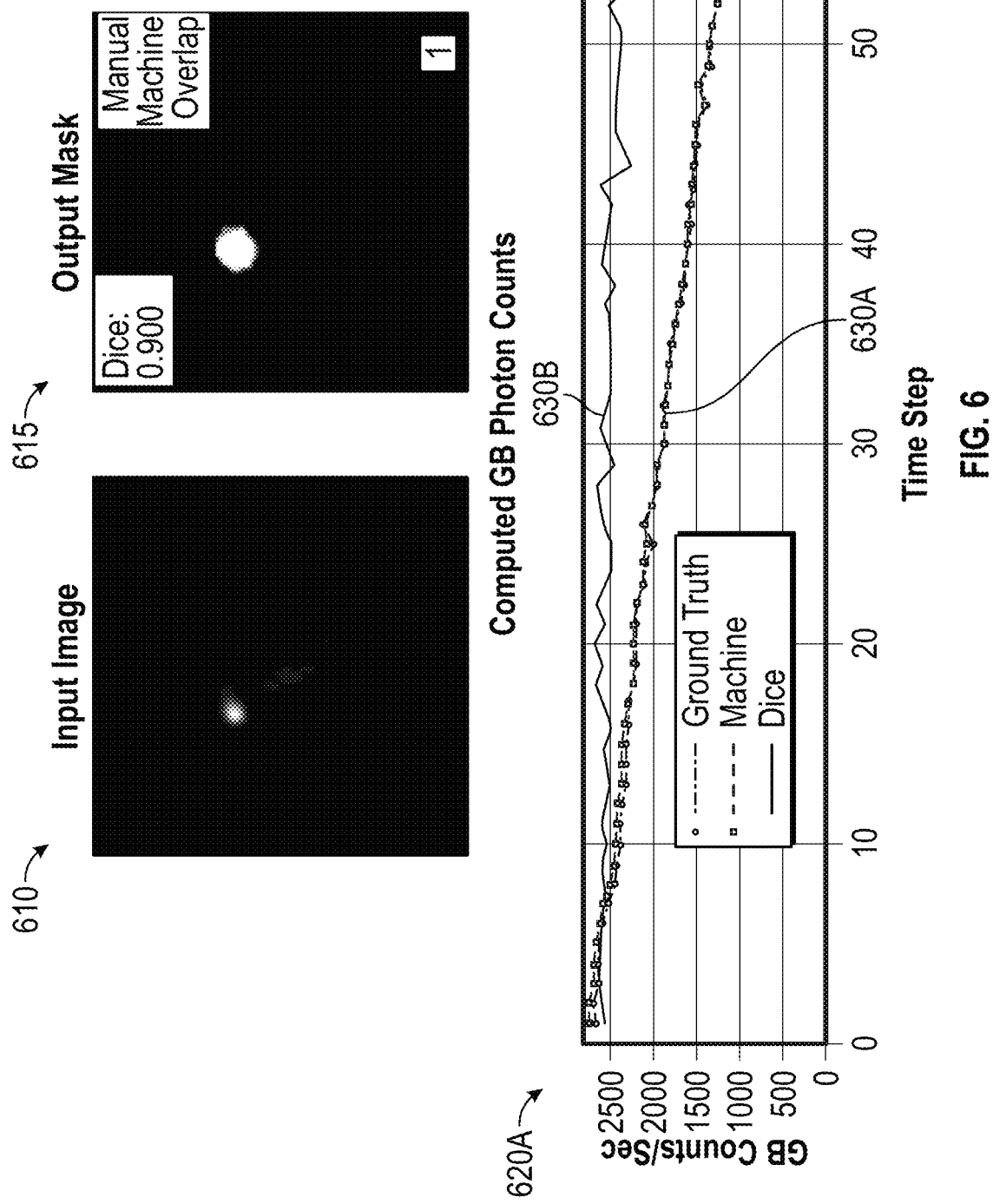
FIG. 6 illustrates results of AI-enabled real time analysis of an image scan according to one particular, non-limiting exemplary embodiment of the disclosed concept.
Figure 6:
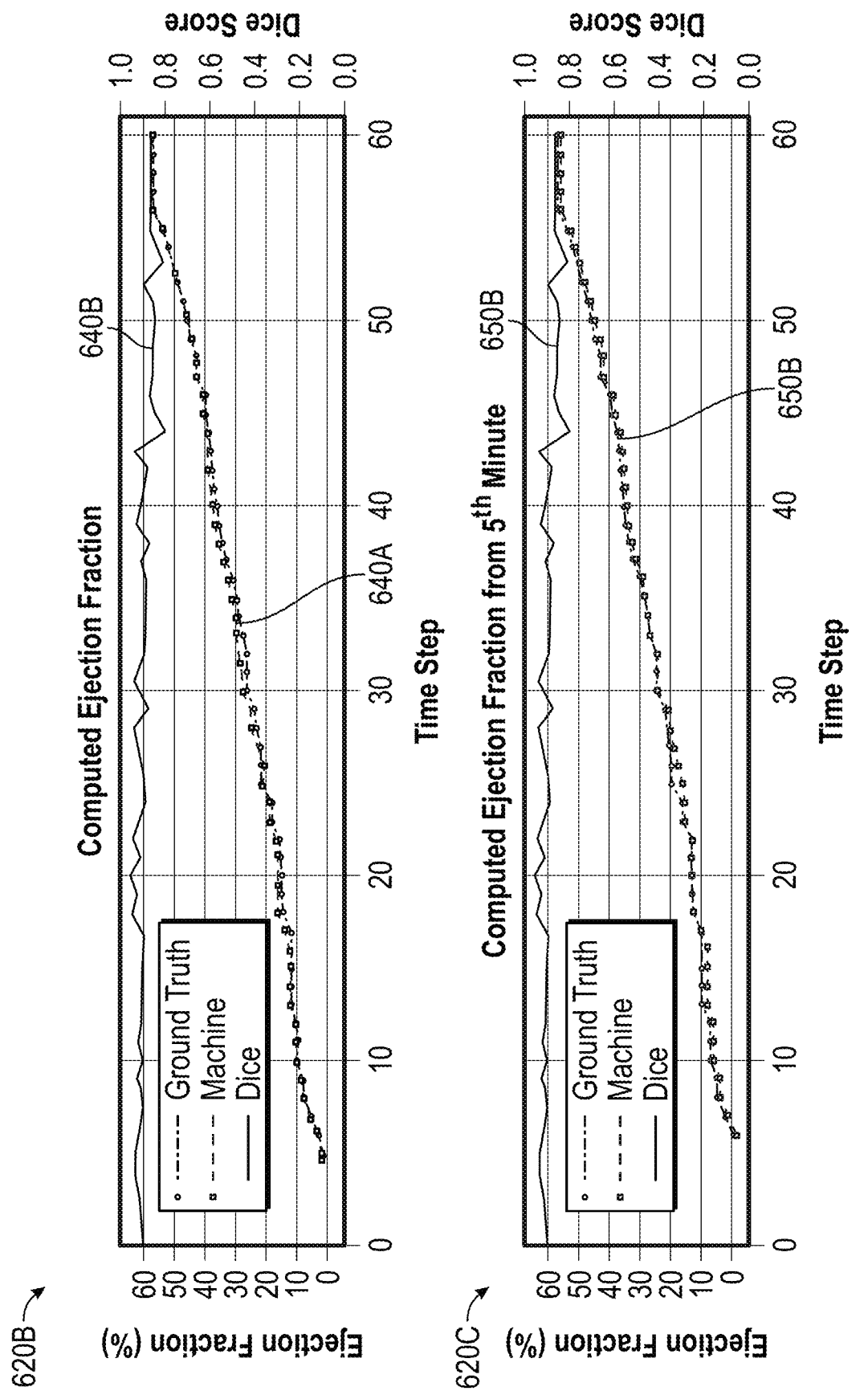

FIG. 6 illustrates results of AI-enabled real time analysis of an image scan according to one particular, non-limiting exemplary embodiment of the disclosed concept. A patient was scanned for 60 min and gallbladder (GB) input image 610 was analyzed by the AI-enabled real time analysis device. The output image 615 with DICE at 0.900 is shown, the ROI function is calculated based on the output image 615, and the AI-enabled real time analysis results 620A-C are shown. The average DICE is 0.894 and EF information from DICOM (digital imaging and communications in medicine) is between 1.5 minutes and 55.5 minutes, which is 54%. At 20 minutes, EF is 14%. At 40 minutes, EF is 33%. At 60 minutes, EF is 52%. In this case, if the predefined EF value set by the user is ≥38%, the imaging must continue for 60 minutes. The graph 620A shows that the computed GB photon counts 630A of ground truth and those counts 630B determined by AI-enabled real time analysis device are almost identical. The graph 620B shows that the computed ejection fractions 640A of ground truth and those EF 640B determined by the real-time, AI-enabled analysis device are almost identical as well. The graph 620C shows that the computed ejection fractions 650A from fifth minute of ground truth and those EF 650B determined by the real-time, AI-enabled analysis device are also almost identical. As such, in an easier case, the ROI function calculation values by the real-time, AI-enabled analysis device were almost identical to the ROI function calculation of the ground truth.

Figure 7:
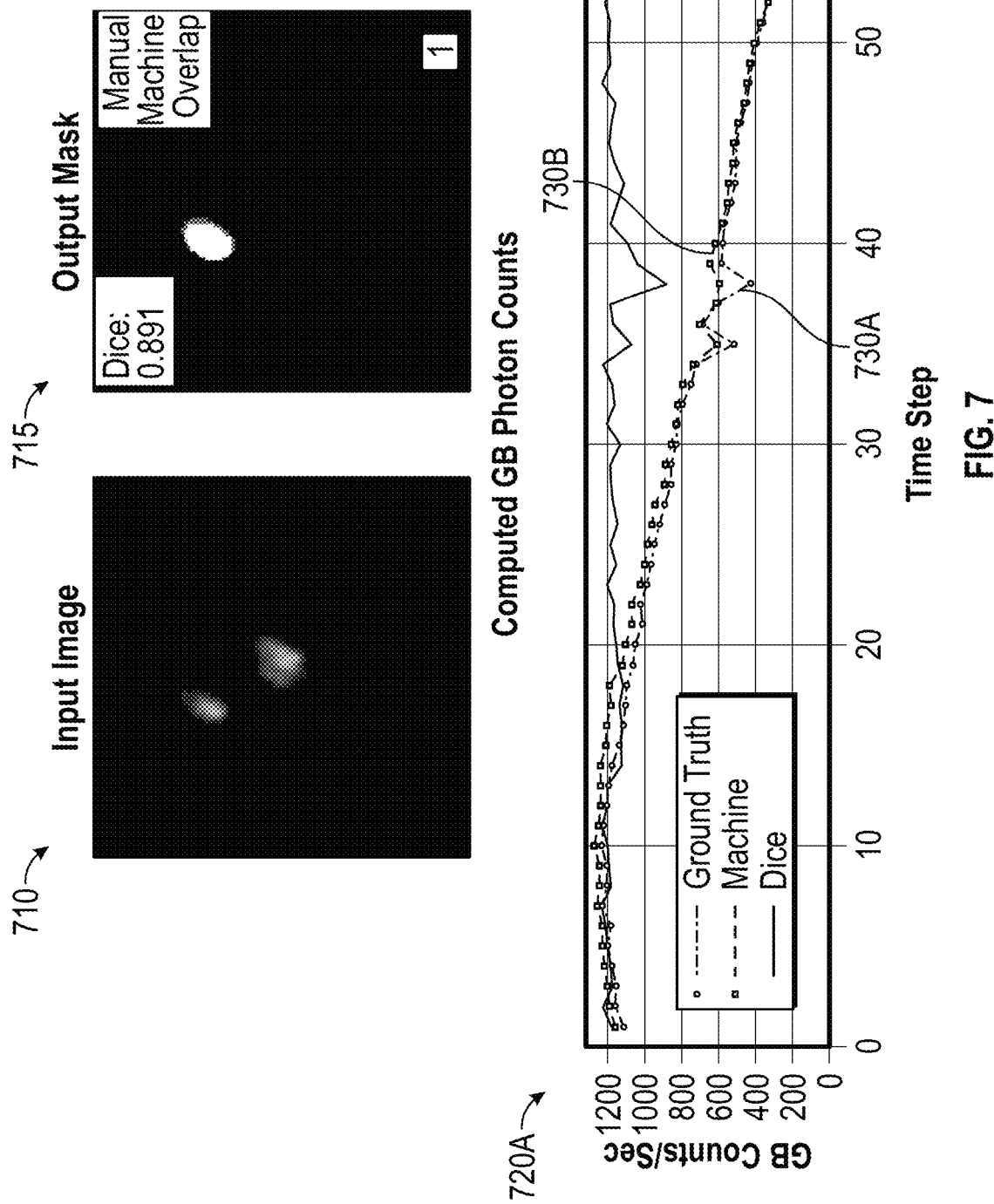
FIG. 7 illustrates results of AI-enabled real time analysis of an image scan according to one particular, non-limiting exemplary embodiment of the disclosed concept.
Figure 7:
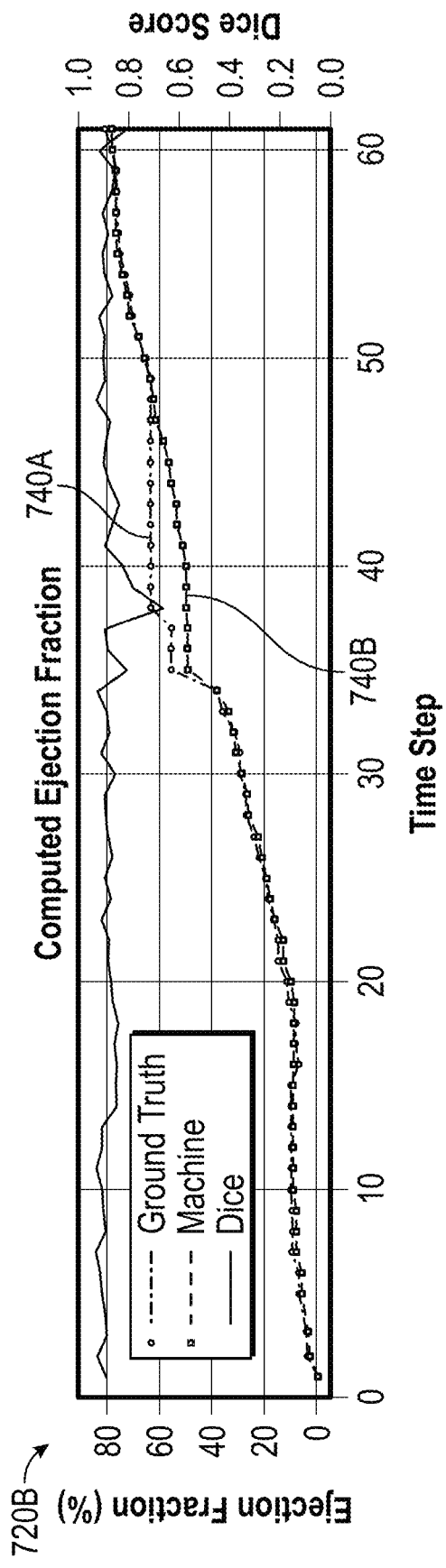
Figure 7:
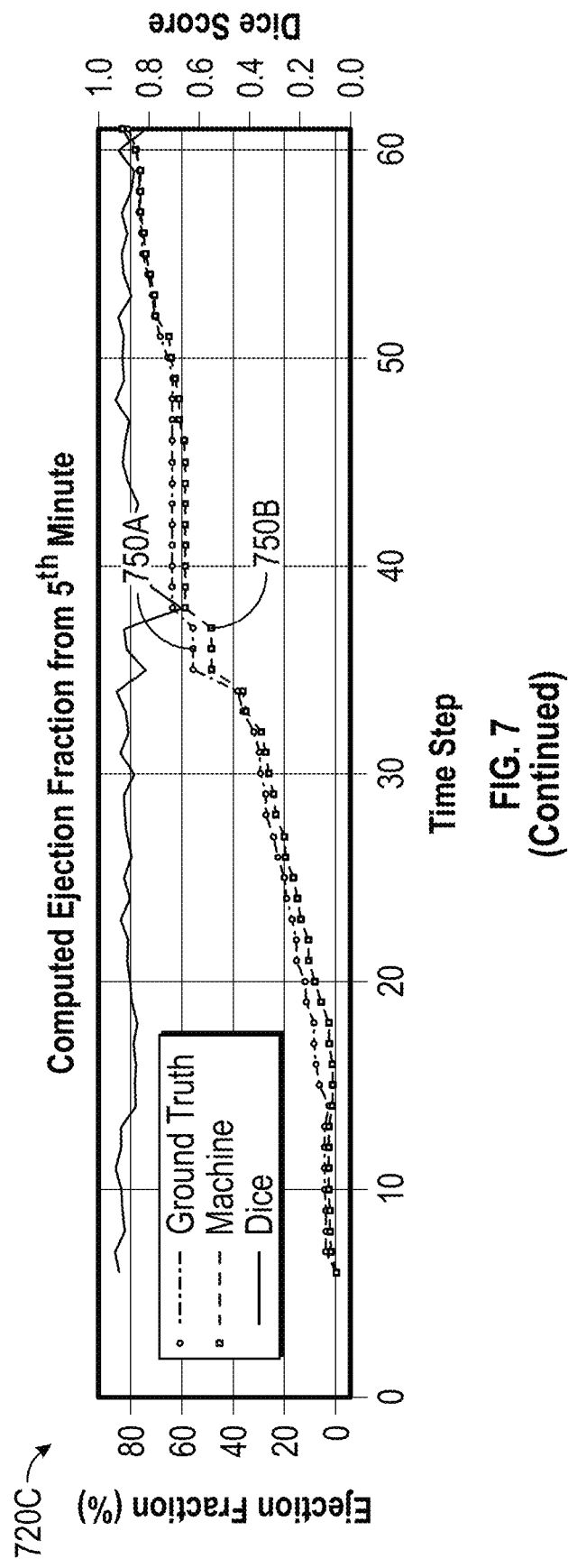

FIG. 7 illustrates results of AI-enabled real time analysis of an image scan according to one particular, non-limiting exemplary embodiment of the disclosed concept. FIG. 7 shows AI-enabled real time analysis results of imaging of another subject in accordance with example embodiment of disclosed concept. The 60-min gallbladder input image 710 was analyzed by the real-time, AI-enabled analysis device in accordance with the present disclosure. The results show that the average dice was 0.878. The output image 715 having dice of 0.891 is shown. The graph 720A shows that computed GB photon counts of the ground truth 730A and those counts 730B calculated by the real-time, AI-enabled analysis device were substantially the same. The graph 720B shows that computed ejection fraction (EF) 740A of the ground truth and those EF 740B calculated by the real-time, AI-enabled analysis device were substantially the same. The graph 720C shows that computed EF 750A from the fifth minute of the ground truth and those 750B calculated by the real-time, AI-enabled analysis device were substantially the same. As such, in a difficult case, the ROI function calculation values by the real-time, AI-enabled analysis device were almost identical to the ROI function calculation of the ground truth.

Figure 8:
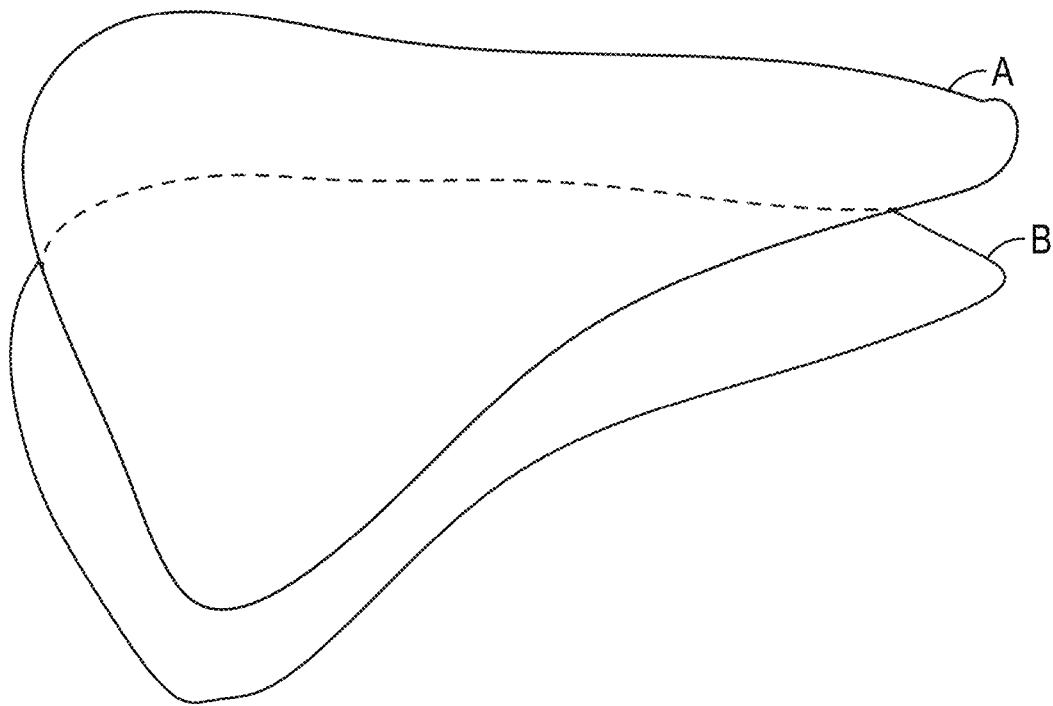
FIG. 8 illustrates example dice outputs according to one particular, non-limiting exemplary embodiment of the disclosed concept.

FIG. 8 illustrates example ROI portions A,B generated according to one particular, non-limiting exemplary embodiment of the disclosed concept. ROI portions A and B are generated using the ROI parameters determined by an AI-enabled data processing system (e.g., the AI-enabled processing system 220 as described with reference to FIG. 2). The portions are correlated using, e.g., Bland-Altman analysis, and the dice similarity coefficient (DSC) is obtained. DSC can be shown as:

$$DSC = 2|A \cap B| / |A| + |B| \qquad \text{EQ. 2}$$

DSC of one means that dices A and B are identical, and DSC of zero means that they have no intersections. Where DSC lies between zero and one, the larger the DSC the better the correlation. As such, DSC may be used to determine, e.g., whether the ML training of the AI-enabled data processing system is complete or not.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An imaging system comprising:
an imaging device comprising a gamma camera and a persistence scope, and structured to scan a subject during an image scan performed by an operator, the subject comprising an organ, a structure, or a region of interest (ROI) of the organ or the structure; and
a real-time, AI-enabled analysis device coupled to the imaging device and comprising an AI-enabled data processing system, an input apparatus, and a display, the real-time, AI-enabled analysis device configured to:
receive data corresponding to a plurality of image frames from the gamma camera and user input identifying the ROI using the persistence scope in a first image frame of the plurality of the image frames;
provide data corresponding to the first image frame, including the identified ROI and data corresponding to the remaining image frames to the AI-enabled data processing system, wherein the AI-enabled data processing system has been previously trained to automatically track the identified ROI during the image scan using training and test data representing a number of image datasets associated with the ROI obtained from a plurality of test subjects;
accept a plurality of valid image frames from the plurality of image frames based on a predefined set of computer vision rules and a minimum accepted frame threshold;
calculate, frame by frame, an ROI function value of the plurality of valid image frames;
automatically determine whether a predetermined ROI function value has been reached; and
alert the operator of the imaging device that at least one of the predetermined ROI function value or a predefined maximum scan duration has been reached.

2. The system of claim 1, wherein the real-time, AI-enabled analysis device is further configured to:
determine whether a request to stop the image scan has been received; and
terminate the image scan based on a determination that the request has been received; or
continue the image scan based on a determination that the request has not been received.

3. The system of claim 1, wherein the real-time, AI-enabled analysis device is configured to accept the plurality of valid image frames by:
setting the first image frame as a baseline image frame and the data corresponding to the first image frame including the identified ROI as baseline image frame data;
setting an image frame immediately following the baseline image frame as a current image frame;
automatically identifying the ROI in the current image frame using the AI-enabled data processing system;
determining whether the current image frame satisfies the predefined set of computer vision rules;
setting the data corresponding to the current image frame including the ROI as a current image frame data based on a determination that the current image frame has satisfied the predefined set of computer vision rules; and
accepting the current image frame as a valid image frame of the plurality of valid image frames based on the determination that the current image frame satisfies the predefined set of computer vision rules.

4. The system of claim 3, wherein the predefined set of computer vision rules comprises a first predefined range associated with a radioactive tracer count within the ROI and a second predefined range associated with a voxel count within the ROI, and the real-time AI-enabled analysis device is configured to accept the current image frame based on:

a determination that the current image frame data is within the first predefined range; and
a determination that the current image frame data is within the second predefined range.

5. The system of claim 3, wherein the real-time, AI-enabled analysis device is further configured to:
exclude the current image frame from calculating the ROI function value based on one of a determination that the current image frame data is not within the first predefined range and a determination that the current image frame data is not within the second predefined range; and
set an image frame immediately following the current image frame as a new current image frame for at least one of automatically the ROI in the new current image frame, accepting the new current image frame, or calculating the ROI function value.

6. The system of claim 3, wherein the real-time, AI-enabled analysis device is further configured to set the current image frame as a new baseline image frame and the image frame immediately following the current image frame as a new current image frame based on a determination that the minimum accepted frame threshold is not met.

7. The system of claim 1, wherein the ROI function value to be calculated comprises at least one of an ejection fraction (EF) or clearance of radioactivity within the ROI.

8. The system of claim 7, wherein the ROI function threshold comprises a preset range of EF percentage or percentage clearance of radioactivity, based at least in part on a type of the image scan.

9. The system of claim 1, wherein the real-time, AI-enabled analysis device is further configured to provide real time feedback comprising a frame-by-frame graphic display of time-activity curve, the ROI function value calculation, or real-time updates associated with the ROI function calculation via the display.

10. The system of claim 1, wherein the real-time, AI-enabled analysis device is couplable to at least one of a USB drive, a hard drive, or a cloud server for receiving real-time, AI-enabled analysis software application, software updates, or training data.

11. A real-time, AI-enabled analysis device coupled to an imaging device for use during an image scan, comprising:
an input apparatus;
a display; and
an AI-enabled data processing system, wherein the real-time, AI-enabled analysis device is configured to:
receive data corresponding to a plurality of image frames from the imaging device and user input identifying an ROI in a first image frame of the plurality of the image frames;
provide data corresponding to the first image frame, including the identified ROI and data corresponding to the remaining image frames to the AI-enabled data processing system, wherein the AI-enabled data processing system has been previously trained to automatically identify the ROI during the image scan using training and test data representing a number of image datasets associated with the ROI obtained from a plurality of test subjects;
accept a plurality of valid image frames from the plurality of image frames based on a predefined set of computer vision rules and a minimum accepted frame threshold;
calculate, frame by frame, an ROI function value of the plurality of valid image frames; and
determine whether a predetermined ROI function value has been reached; and
alert an operator of the imaging device that the predetermined ROI function value has been reached.

12. A method of imaging using a real-time, AI-enabled analysis device coupled to an imaging device during an image scan of a subject, comprising:
receiving data corresponding to a plurality of image frames from the imaging device and user input identifying a region of interest (ROI) in a first image frame of the plurality of the image frames;
providing data corresponding to the first image frame, including the identified ROI and data corresponding to the remaining image frames to an AI-enabled data processing system of the real-time, AI-enabled analysis device, wherein the AI-enabled data processing system has been previously trained automatically to track the identified ROI during the image scan using training and test data representing a number of image datasets associated with the ROI obtained from a plurality of test subjects;
accepting a plurality of valid image frames from the plurality of image frames based on a predefined set of computer vision rules and a minimum accepted frame threshold;
calculating, frame by frame, an ROI function value of the plurality of valid image frames;
determining whether a predetermined ROI function value has been reached; and
alerting an operator of the imaging device that the predetermined ROI function value has been reached.

13. The method of claim 12, further comprising:
determining whether a request to terminate the image scan from the operator has been received; and
terminating the image scan based on a determination that the request has been received and displaying the scan results on a display of the real-time, AI-enabled analysis device; or
continuing the image scan based on a determination that the request has not been received.

14. The method of claim 12, wherein the accepting the plurality of valid image frames comprises:
setting the first image frame as a baseline image frame and the data corresponding to the first image frame including the identified ROI as baseline image frame data;
setting an image frame immediately following the baseline image frame as a current image frame;
automatically identifying the ROI in the current image frame using the AI-enabled data processing system;
determining whether the current image frame satisfies the predefined set of computer vision rules;
setting the data corresponding to the current image frame including the ROI as a current image frame data based on the determination that the current image frame satisfies the predefined set of computer vision rules; and
accepting the current image frame as a valid frame image of the plurality of valid frame images based on the determination that the current image frame satisfies the predefined set of computer vision rules.

15. The method of claim 14, wherein the predefined set of rules comprises a first predefined range associated with a radioactive tracer count within the ROI and a second predefined range associated with a voxel count within the ROI, and the accepting the current image frame is based on:
a determination that the current image frame data is within the first predefined range; and a determination that the current image frame data is within the second predefined range.

16. The method of claim 12, wherein the predefined set of rules comprises a first predefined range associated with a radioactive tracer count within the ROI and a second predefined range associated with a voxel count within the ROI, the method further comprising:
excluding the current image frame from calculating the ROI function value based on one of a determination that the current image frame data is not within the first predefined range or a determination that the current image frame data is not within the second predefined range; and
setting an image frame immediately following the current image frame as a new current image frame for at least one of automatically identifying the ROI in the new current image frame by the AI-enabled data processing system, accepting the new current image frame, or calculating the ROI function value.

17. The method of claim 14, wherein the real-time, AI-enabled analysis device is further configured to set the current image frame as a new baseline image frame and the image frame immediately following the current image frame as a new current image frame based on a determination that the minimum accepted frame threshold is not met.

18. The method of claim 12, wherein the ROI function value to be calculated comprises at least one of an ejection fraction (EF) and a clearance of radioactivity within the ROI.

19. The method of claim 12, wherein the ROI function threshold comprises a preset range of percentage of the EF percentage or clearance percentage based on a type of the subject for the image scan.

20. The method of claim 12, further comprising:
providing real time feedback comprising a frame-by-frame graphic display of time-activity curve, the ROI function value calculation, or real-time updates associated with the ROI function value calculation via the display.

* * * * *